(12) United States Patent
Yeh et al.

(10) Patent No.: US 6,614,694 B1
(45) Date of Patent: Sep. 2, 2003

(54) ERASE SCHEME FOR NON-VOLATILE MEMORY

(75) Inventors: Chih-Chieh Yeh, Taipei (TW); Wen-Jer Tsai, Hualien (TW); Tao-Cheng Lu, Kaohsiung (TW)

(73) Assignee: Macronix International Co., Ltd., Hsin-Chu (TW)

( * ) Notice: Subject to any disclaimer, the term of this patent is extended or adjusted under 35 U.S.C. 154(b) by 0 days.

(21) Appl. No.: 10/112,707

(22) Filed: Apr. 2, 2002

(51) Int. Cl.[7] .............................................. G11C 16/04
(52) U.S. Cl. .......................... 365/185.29; 365/185.18; 365/185.3; 365/185.26; 365/185.24
(58) Field of Search ...................... 365/185.29, 185.18, 365/185.3, 185.26, 185.24

(56) References Cited

U.S. PATENT DOCUMENTS

| | | |
|---|---|---|
| 5,768,192 A | 6/1998 | Eitan |
| 6,034,896 A * | 3/2000 | Ranaweera et al. ..... 365/185.28 |
| 6,512,696 B1 * | 1/2003 | Fan et al. ............... 365/185.18 |
| 2003/0036250 A1 * | 2/2003 | Lin et al. .................... 438/466 |

* cited by examiner

*Primary Examiner*—Richard Elms
*Assistant Examiner*—Toan Le
(74) *Attorney, Agent, or Firm*—Birch, Stewart, Kolasch & Birch, LLP

(57) ABSTRACT

A method of an erase scheme for a non-volatile memory cell. The non-volatile memory cell includes a substrate, source, drain with a channel region and a gate above the channel region separated by nonconducting charge-trapping material sandwiched between first and second insulating layers. The method includes the following steps. First, hot hole erase is performed to inject hot holes into the nonconducting charge-trapping material to eliminate first electrons trapped in the nonconducting charge-trapping material and causing some holes to remain in the second insulating layer. Finally, soft anneal is performed to inject second electrons to the second insulating layer to eliminate the holes left in the second insulating layer.

20 Claims, 4 Drawing Sheets

ERASE SCHEME FOR NON-VOLATILE MEMORY

BACKGROUND OF THE INVENTION

1. Field of the Invention

The present invention relates generally to semiconductor memory devices and more particularly to an erase scheme for a programmable read only memory (PROM) cell having charge trapping dielectric material in the gate.

2. Description of the Related Art

Memory devices for non-volatile storage of information are currently in widespread use today, being used in a myriad of applications.

U.S. Pat. No. 5,768,192, issued to Eitan et al., teaches an apparatus and method of programming and reading a programmable read only memory (PROM) having a trapping dielectric layer sandwiched between two silicon dioxide layers, as shown in FIG. 1. FIG. 1 illustrates a sectional view of a PROM cell constructed in accordance with Eitan's reference utilizing ONO as the gate dielectric. The PROM can be programmed to let electrons trapped in both sides of the silicon nitride layer 20 near the source 14 and the drain 16 (i.e. 2 bits/cell operation).

The operation of erasing data restored in the device is described. A conventional erase method is band-to-band hot-hole erase. If the silicon dioxide layer 18 is thick, for example, 20 nm or thicker, an FN tunneling current has difficulty flowing unless the voltage between the gate 24 and n-type region 14 or 16 becomes high. Therefore, the potential difference between the n-type region 14 or 16 and channel region becomes large earlier than between the n-type region 14 or 16 and gate electrode 24 and an avalanche breakdown occurs at the end portion of the n-type region 14 or 16.

Hot holes generated by the electrons band-to band tunneling are accelerated by the electric field in the depletion layer. When the hot holes obtain a sufficiently high energy, they are injected toward the gate 24 maintained at the low potential and trapped in the silicon nitride layer 20. Since electrons are trapped beforehand in the silicon nitride layer 20, electrons and holes are recombined to erase the stored data.

However, band-to-band hot-hole erase will result in serious read disturb which may come from the residual hole traps in silicon dioxide layer 18 assisting electron tunneling and channel shortening enhancing lateral field. Serious read disturb may also cause window closure and can be an issue for device scaling.

SUMMARY OF THE INVENTION

The object of the present invention is to perform a soft anneal after band-to-band hot-hole erase. The soft anneal reduces the read disturb effect by eliminating the hole traps in oxide and restoring the shortened channel induced by over erasure. Therefore, device scaling is achievable.

To achieve the above-mentioned object, the present invention provides a method of an erase scheme for a non-volatile memory cell. The non-volatile memory cell includes a substrate, source, drain with a channel region and a gate above the channel region separated by nonconducting charge-trapping material sandwiched between first and second silicon dioxide layers. The method includes the following steps. First, hot hole erase is performed to inject hot holes into the nonconducting charge-trapping material to eliminate first electrons trapped in the nonconducting charge-trapping material and causing some holes to remain in the second silicon dioxide layer. Finally, soft anneal is performed to detrap the holes left in the second silicon dioxide layer or to inject second electrons to the second silicon dioxide layer to eliminate the holes left in the second silicon dioxide layer.

BRIEF DESCRIPTION OF THE DRAWINGS

The present invention will become more fully understood from the detailed description given hereinbelow and the accompanying drawings, given by way of illustration only and thus not intended to be limitative of the present invention.

DETAILED DESCRIPTION OF THE PREFERRED EMBODIMENT

Figure 1:
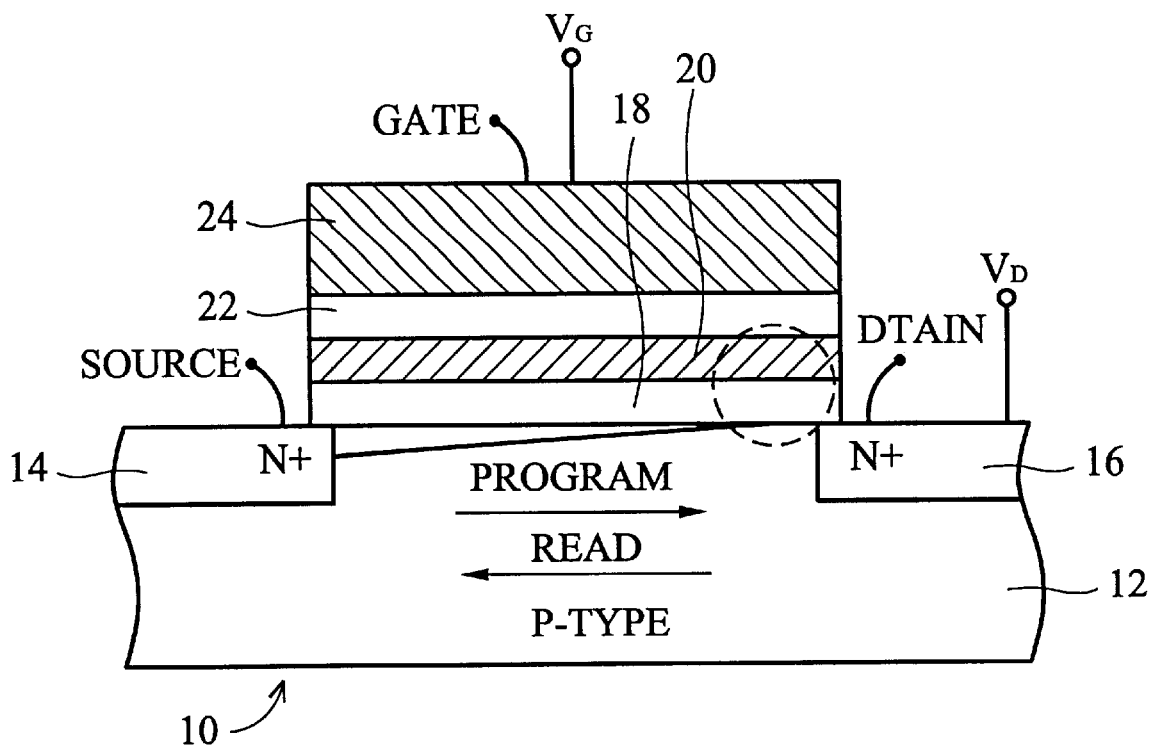
FIG. 1 illustrates a sectional view of a PROM cell constructed in accordance with Eitan's reference utilizing ONO as the gate dielectric.
Figure 2:
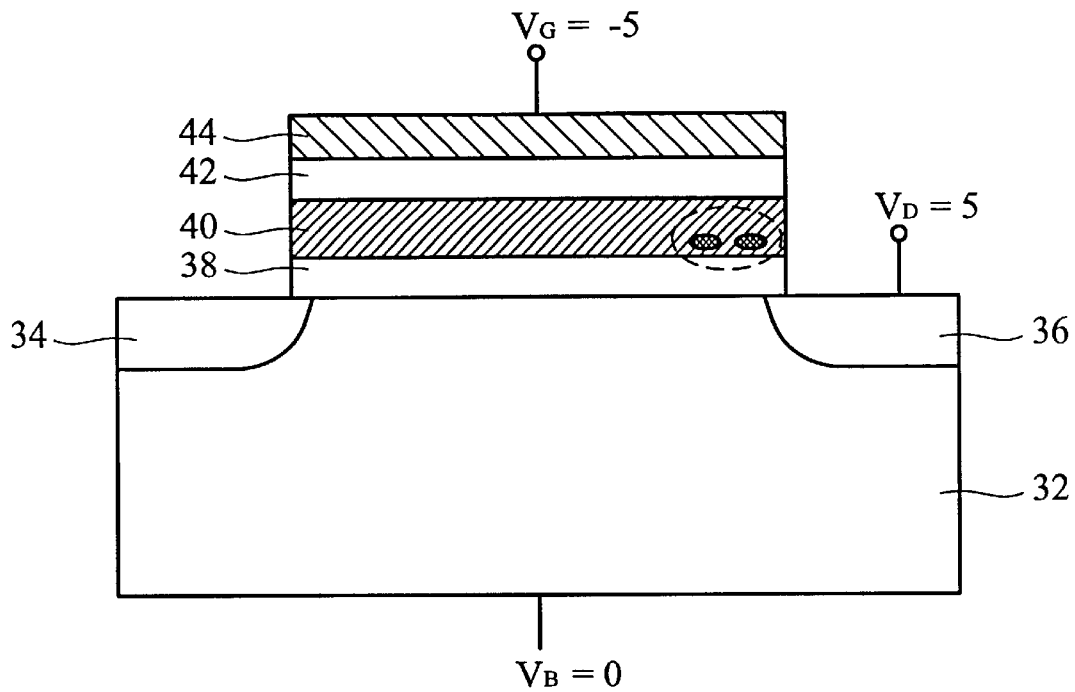
FIG. 2 illustrates a sectional view of a PROM cell constructed in accordance with the embodiment of the present invention, the bias is applied during band-to-band hot-hole erase.

FIG. 2 illustrates a sectional view of a PROM cell constructed in accordance with the embodiment of the present invention, the bias is applied during band-to-band hot-hole erase.

A P-type substrate 32 has two buried N+ junctions, one being the source 34 and the other being the drain 36. Above the channel region is a layer of silicon dioxide 38, preferably between approximately 80–100 angstroms thick, which forms an electrical isolation layer over the channel region. On top of the silicon dioxide layer 38 is a silicon nitride layer 40 preferably approximately 100 angstroms thick. This silicon nitride 40 layer forms the memory retention layer functioning to trap the hot electrons as they are injected into the nitride layer 40. Another layer of silicon dioxide 42 is formed over the silicon nitride layer 40 and is preferably between approximately 80–100 angstroms thick. The silicon dioxide layer 42 functions to electrically isolate a conductive gate 44 formed over the silicon dioxide layer 42. The layer forming the gate 44 can be constructed from polycrystalline silicon, commonly known as polysilicon.

When the PROM memory cell is programmed, voltages are applied to the gate 44 and drain 36 creating vertical and lateral electrical fields, which accelerate the electrons along the length of the channel region. As the electrons move along the channel some of them gain sufficient energy to jump over the potential barrier of the bottom silicon dioxide layer 38 and become trapped in the silicon nitride layer 40. The electron trapping occurs in a region near the drain indicated by the dashed circle in FIG. 2. Electrons are trapped near the drain region 36 because the electric fields are the strongest there, thus the electrons have a maximum probability of being sufficiently energized to jump the potential barrier and become trapped in the nitride layer 40. The threshold voltage of the portion of the gate over the trapped charge increases as more electrons are injected into the nitride layer.

Because the silicon nitride layer 40 is not conductive material, the electrons can be trapped in both sides of the silicon nitride layer 40 near the source 34 and the drain 36, which means 2 bits/cell operation.

Band-to-band hot-hole erase is used for the erase operation of the non-volatile memory according to the present invention.

Hot holes generated by electrons band-to-band tunneling are accelerated by the electric field in the depletion layer. Here, the source/drain 36 is applied with positive bias range from 3 to 10 volts, and the gate 44 is applied with negative bias range from 0 to −10 volts.

When the hot holes obtain a sufficiently high energy, they are injected toward the gate 44 maintained at the low potential and trapped in the silicon nitride layer 40. Since electrons are trapped beforehand in the silicon nitride layer 40, electrons and holes are recombined or compensated to erase the stored data.

Since band-to-band hot-hole erase results in serious read disturb which may come from the residual hole traps in silicon dioxide layer 38 assisting electron tunneling and channel shortening enhancing lateral field, soft-program anneal is performed after band-to-band hot-hole erase.

Figure 3:
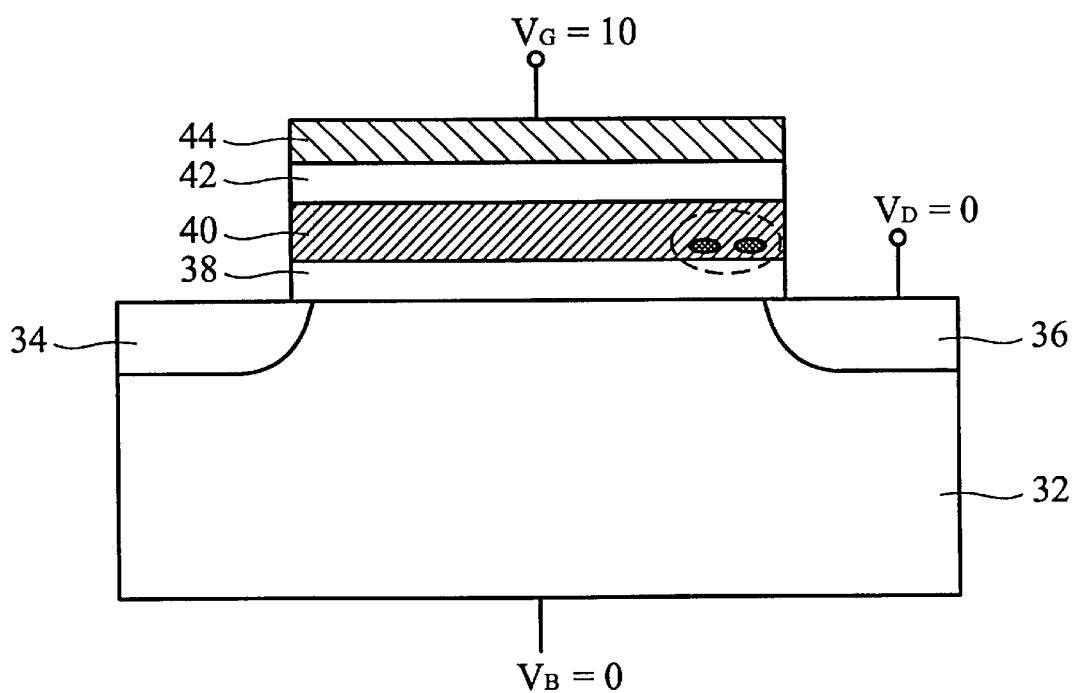
FIG. 3 illustrates a sectional view of a PROM cell constructed in accordance with the embodiment of the present invention, the bias is applied during soft-program anneal.

FIG. 3 illustrates a sectional view of a PROM cell constructed in accordance with the embodiment of the present invention, the bias applied during soft-program anneal.

Soft anneal is achieved by detrapping residual hole traps or injecting electrons to the silicon dioxide layer 38 to recombine with the residual holes by large electric field assisted tunneling effect. A positive voltage (9–10V) is directly applied to the gate 44 for detrapping the residual hole traps or driving the electrons in the substrate 32 to tunnel the silicon dioxide layer 38 to recombine or compensate with the residual hole traps in the silicon dioxide layer 38. Here, the source bias, drain bias, and substrate bias are 0V, and Soft anneal is performed for 50 ms. Moreover, soft anneal is also achieved by grounding the source/drain 34, applying the voltage range from 0 to 8 volts to the source/drain 36 and applying the voltage range from 3 to 13 volts to the gate 44.

Figure 4:
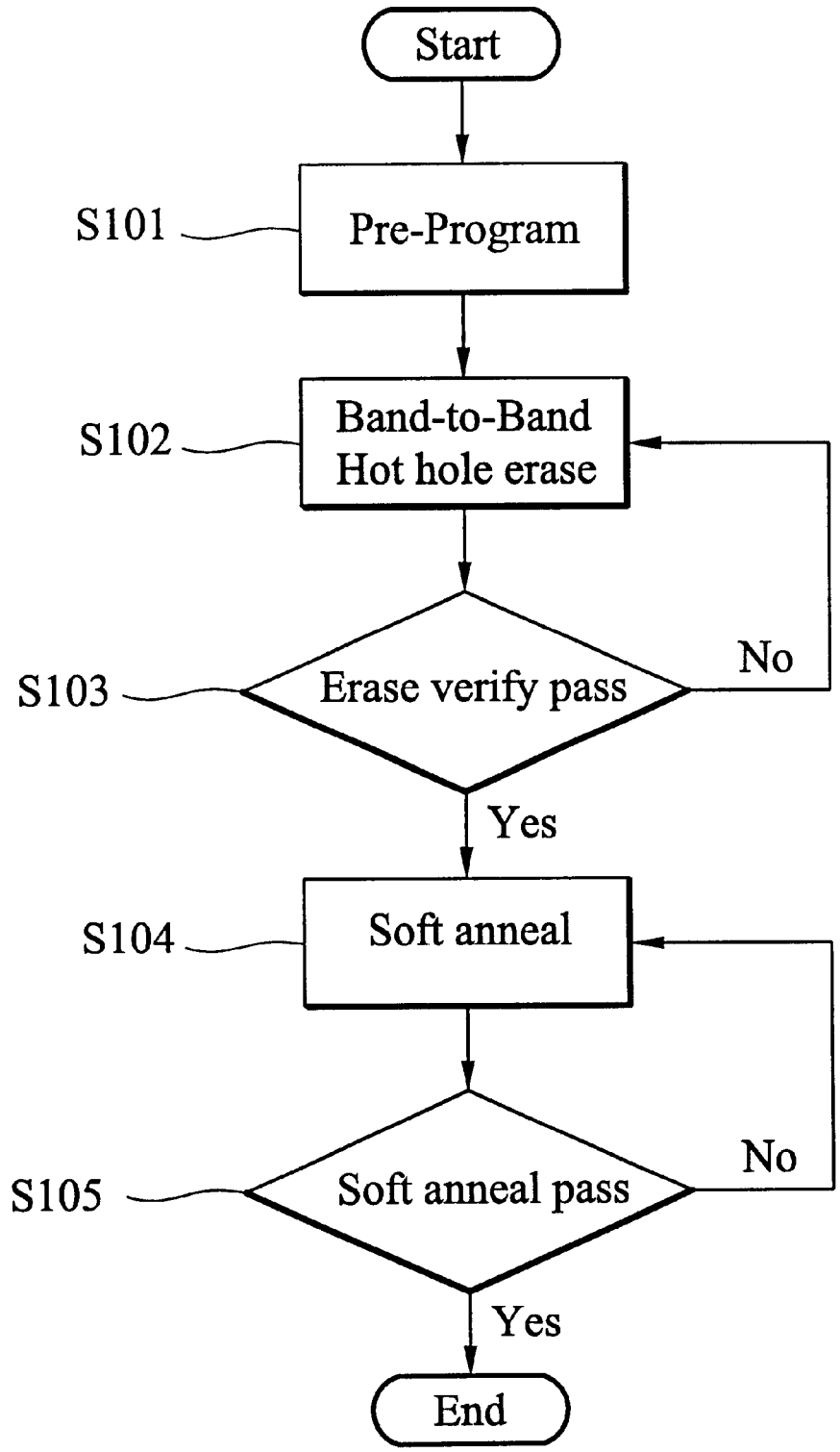
FIG. 4 is a flow chart of the erase operation according to the embodiment of the present invention.

FIG. 4 is a flow chart of the erase operation according to the embodiment of the present invention.

First, Pre-program is performed to raise the threshold voltage of memory cells to avoid over erasing (S101). Next, band-to-band hot-hole erase is performed to eliminate the electrons trapped in the memory cell (S102). Therefore, the threshold voltage of memory cells is low potential. Next, a verification step of hot hole erase is performed to ensure the memory device is erased to the desired level (S103). If erase verification is not passed, the process goes back to step S102. If erase verification is passed, the process goes to step S104. At step S104, soft anneal is performed to anneal the damaged device. In the present embodiment, soft anneal can be performed by FN injection, hot carrier injection, and secondary hot carrier injection. Next, a verification step is implemented after soft anneal in the erase algorithm to check the completion of the anneal step (S105).

Figure 5:
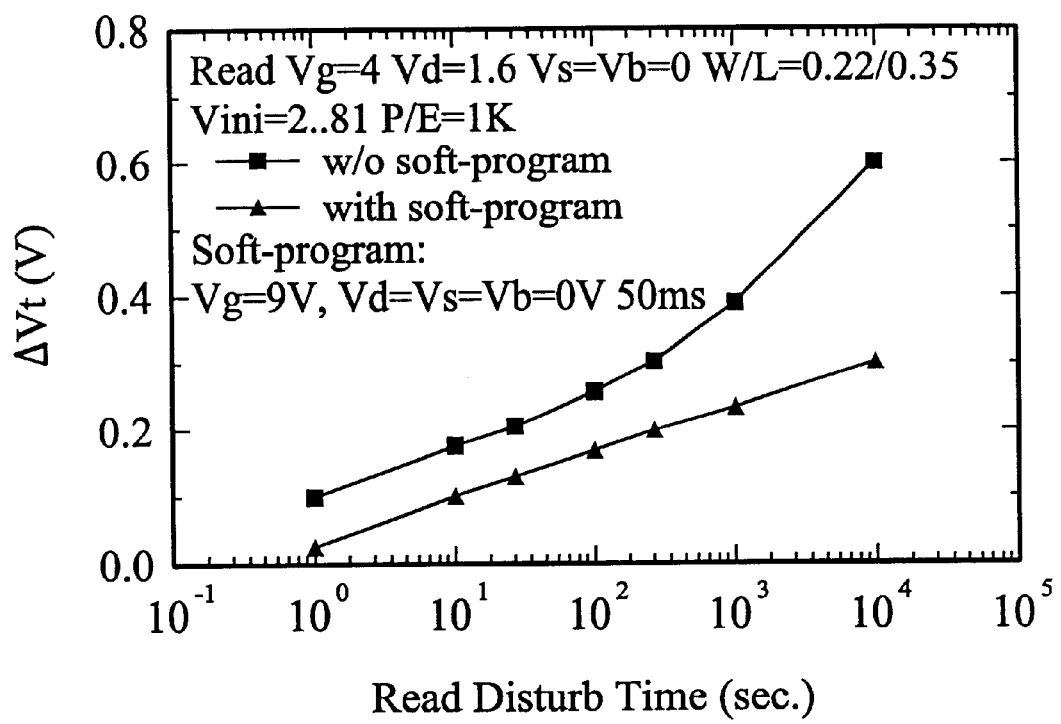
FIG. 5 shows a chart of the variation of threshold voltage $\Delta Vt$ against read disturb time.

FIG. 5 shows a chart of the variation of threshold voltage ΔVt against read disturb time. As shown in FIG. 5, the read disturb is largely improved after implementing the soft anneal.

Accordingly, the present invention involves an additional soft anneal step to fix the device damaged by hot-hole erase. With the applied soft anneal, holes are compensated, detrapped or recombined. Fewer hole traps reduce both read disturb and programmed state charge loss and achieve better retentive characteristics. As well, FN soft-anneal is a quick, low-power operation that can be easily designed and implemented.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A method of an erase scheme for a non-volatile memory cell, comprising the following steps:

performing hot hole erase to inject hot holes into the non-volatile memory cell to eliminate first electrons trapped in the non-volatile memory cell, wherein some holes remain in the non-volatile memory cell; and performing soft anneal to eliminate the holes left in the non-volatile memory cell.

2. The method of an erase scheme for a non-volatile memory cell as claimed in claim 1, wherein soft anneal is achieved by injecting second electrons to the non-volatile memory cell.

3. The method of an erase scheme for a non-volatile memory cell as claimed in claim 1, wherein soft anneal is achieved by detrapping the holes left in the non-volatile memory cell.

4. A method of an erase scheme for a non-volatile memory cell, the non-volatile memory cell having a substrate, first source/drain, second source/drain with a channel region therebetween, and a gate above the channel region separated therefrom by nonconducting charge-trapping material sandwiched between first and second insulating layers, the method comprising the following steps:

performing hot hole erase to inject hot holes into the nonconducting charge-trapping material to eliminate first electrons trapped in the nonconducting charge-trapping material, wherein some holes remain in the second insulating layer; and performing soft anneal to eliminate the holes left in the second insulating layer.

5. The method of an erase scheme for a non-volatile memory cell as claimed in claim 4, wherein the second source/drain is applied with positive bias during hot hole erase.

6. The method of an erase scheme for a non-volatile memory cell as claimed in claim 5, wherein the positive bias is range from 3 to 10 volts.

7. The method of an erase scheme for a non-volatile memory cell as claimed in claim 4, wherein the gate is applied with negative bias during hot hole erase.

8. The method of an erase scheme for a non-volatile memory cell as claimed in claim 7, wherein the negative bias is range from 0 to −10 volts.

9. The method of an erase scheme for a non-volatile memory cell as claimed in claim 4, wherein the substrate, first source/drain, and second source/drain are grounded during soft anneal.

10. The method of an erase scheme for a non-volatile memory cell as claimed in claim 4, wherein the substrate and the first source/drain are grounded, and the voltage applied to the second source/drain is range from 0 to 8 volts during soft anneal.

11. The method of an erase scheme for a non-volatile memory cell as claimed in claim 4, wherein the gate is applied with positive bias during soft anneal.

12. The method of an erase scheme for a non-volatile memory cell as claimed in claim 11, wherein the positive bias is range from 3 to 13 volts.

13. A method of an erase scheme for a non-volatile memory cell, the non-volatile memory cell having a substrate, first source/drain, second source/drain with a channel region therebetween, and a gate above the channel region separated therefrom by nonconducting charge-trapping material sandwiched between first and second insulating layers, the method comprising the following steps:

performing pre-program to raise the threshold voltage of the non-volatile memory cell;

performing hot hole erase to inject hot holes into the nonconducting charge-trapping material to eliminate first electrons trapped in the nonconducting charge-trapping material, wherein some holes remain in the second insulating layer; and performing soft anneal to inject second electrons to the second insulating layer to eliminate the holes left in the second insulating layer.

14. The method of an erase scheme for a non-volatile memory cell as claimed in claim 13, further comprising the step of verifying to ensure the threshold voltage of the non-volatile memory cell is erased to the desired level.

15. The method of an erase scheme for a non-volatile memory cell as claimed in claim 13, further comprising the step of verifying the completion of soft anneal.

16. The method of an erase scheme for a non-volatile memory cell as claimed in claim 13, wherein the second source/drain is applied with positive bias during hot hole erase.

17. The method of an erase scheme for a non-volatile memory cell as claimed in claim 13, wherein the gate is applied with negative bias during hot hole erase.

18. The method of an erase scheme for a non-volatile memory cell as claimed in claim 13, wherein the substrate, first source/drain, and second source/drain are grounded during soft anneal.

19. The method of an erase scheme for a non-volatile memory cell as claimed in claim 13, wherein the substrate and the first source/drain are grounded, and the second source/drain is applied with positive bias during soft anneal.

20. The method of an erase scheme for a non-volatile memory cell as claimed in claim 18, wherein the gate is applied with positive bias during soft anneal.

* * * * *